(12) United States Patent
Kretschmann et al.

(10) Patent No.: US 8,313,699 B2
(45) Date of Patent: Nov. 20, 2012

(54) STERILIZATION TESTING DEVICE

(76) Inventors: Harald Kretschmann, Fernwald (DE); Andreas Rauch, Lich (DE)

( * ) Notice: Subject to any disclaimer, the term of this patent is extended or adjusted under 35 U.S.C. 154(b) by 1140 days.

(21) Appl. No.: 10/552,752

(22) PCT Filed: Apr. 8, 2004

(86) PCT No.: PCT/DE2004/000758
§ 371 (c)(1),
(2), (4) Date: Oct. 11, 2005

(87) PCT Pub. No.: WO2004/091672
PCT Pub. Date: Oct. 28, 2004

(65) Prior Publication Data
US 2006/0188393 A1 Aug. 24, 2006

(30) Foreign Application Priority Data
Apr. 10, 2003 (DE) .................................. 103 16 690
Feb. 3, 2004 (DE) .......................... 10 2004 005 377

(51) Int. Cl.
*G01J 1/48* (2006.01)
(52) U.S. Cl. ................ 422/86; 422/26; 422/27; 422/28; 422/50; 422/400; 422/401; 422/420; 422/421; 422/422; 422/423; 422/424; 422/425; 422/426; 422/427; 422/428; 422/429; 422/68.1; 422/82.05; 422/82.06; 436/164; 436/169; 436/170; 435/13; 435/283.1; 435/287.1; 435/287.7; 435/287.8; 435/287.9; 435/288.7
(58) Field of Classification Search ...................... 422/56, 422/58, 26, 27, 28, 50, 86, 400, 401, 420, 422/421, 422, 423, 424, 425, 426, 427, 428, 422/429, 68.1, 82.05, 82.06; 436/164, 169, 436/170; 435/13, 283.1, 287.1, 287.7, 287.8, 435/287.9, 288.7
See application file for complete search history.

(56) References Cited

U.S. PATENT DOCUMENTS

| 4,596,696 | A | | 6/1986 | Scoville, Jr. |
| 5,750,184 | A | * | 5/1998 | Imburgia .................... 427/2.13 |
| 5,824,553 | A | * | 10/1998 | McCormick et al. ............. 436/1 |
| 6,488,890 | B1 | * | 12/2002 | Kirckof .......................... 422/56 |

FOREIGN PATENT DOCUMENTS

| DE | 4 319 397 | 4/1995 |
| DE | 19724158 | 12/1998 |
| DE | 102 13 066 | 8/2003 |
| EP | 0 069 037 | 1/1983 |
| EP | 421760 | 4/1991 |
| EP | 1 308 175 | 5/2003 |
| WO | WO-01/56618 | 8/2001 |

* cited by examiner

*Primary Examiner* — Dennis M White
(74) *Attorney, Agent, or Firm* — Jordan and Hamburg LLP

(57) ABSTRACT

The invention relates to a sterilization testing device comprised of a housing with a test chamber, an indicator placed therein, and with a supply for supplying the sterilization medium. According to the invention, the sterilization testing device consists of at least two housing parts that are matched to one another. A supply channel is made inside the housing part and serves to supply the sterilization medium. The supply channel is configured in such a manner that it forms the base body of the test chamber. The test chamber accommodates the indicator that indicates the completion of the sterilization process. Alternatively to this solution, the invention provides a variant, which is very effective with regard to manufacturing and which permits a quantitative statement regarding the sterilization. Webs are formed inside the housing in the at least partially meandering and/or spiral configuration of the supply channel. These webs, together with, at least in part, the lateral part(s) of the housing parts form a portion of the supply channel. A supply channel formed in this manner accommodates the indicator.

21 Claims, 15 Drawing Sheets

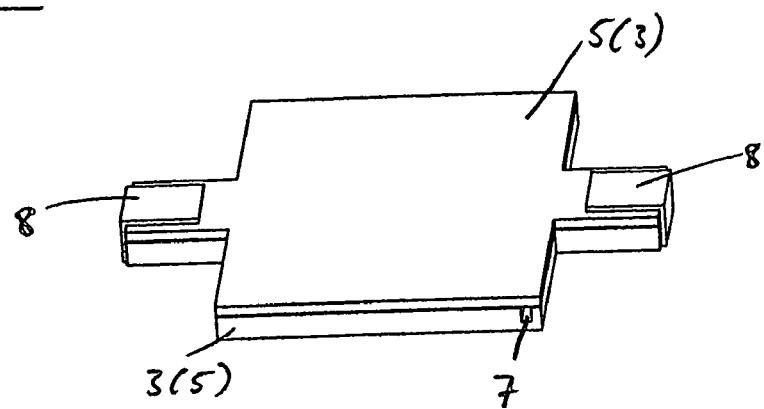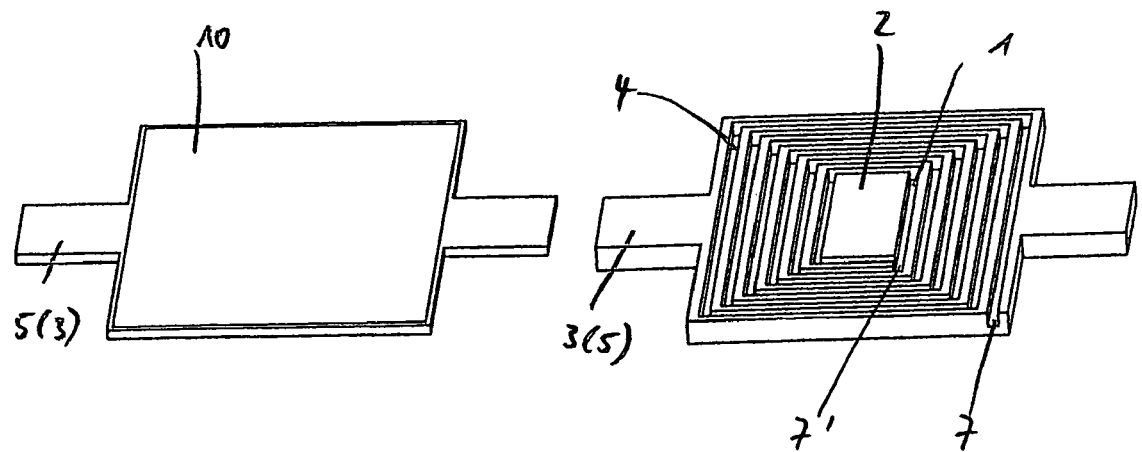

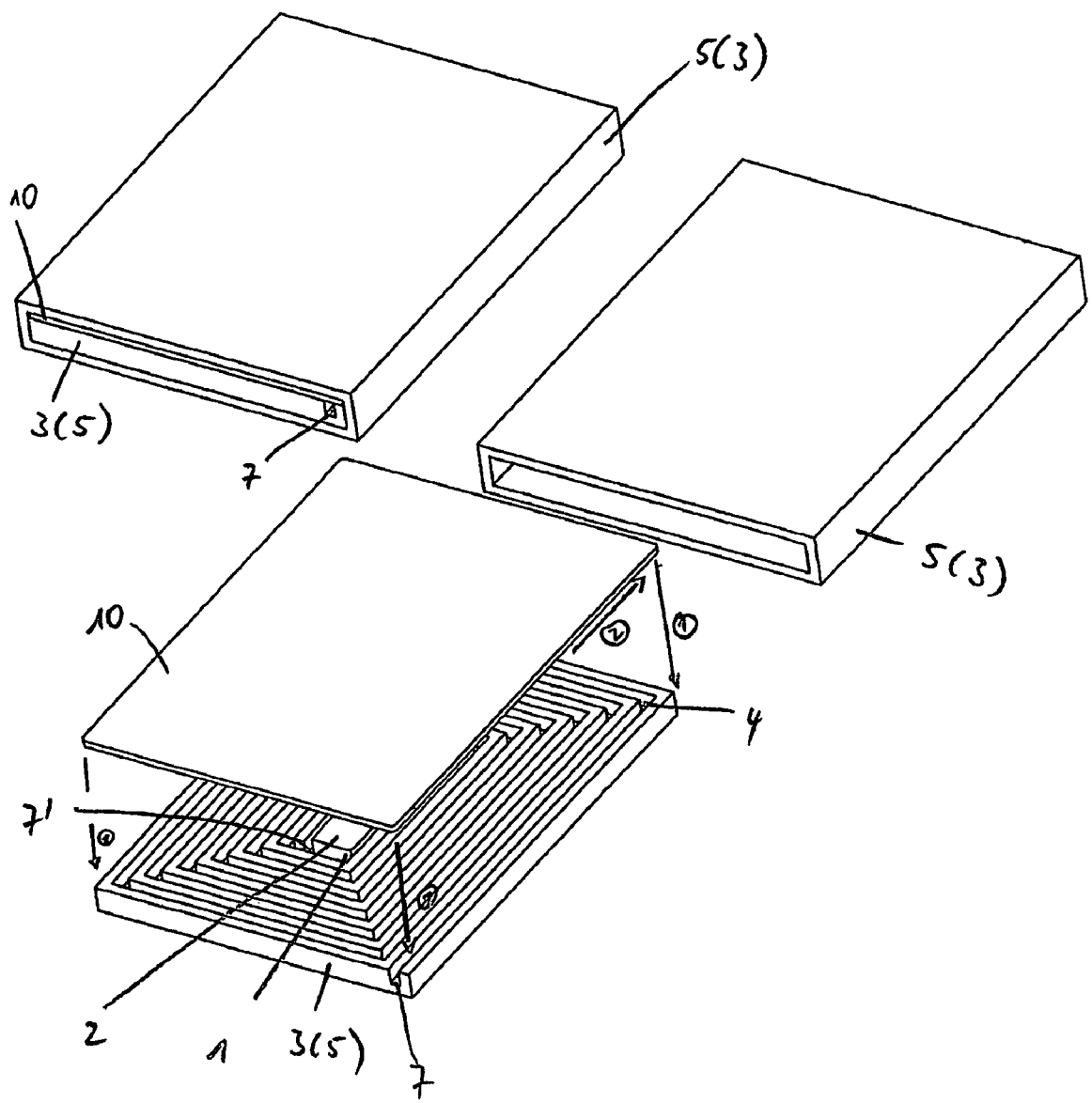

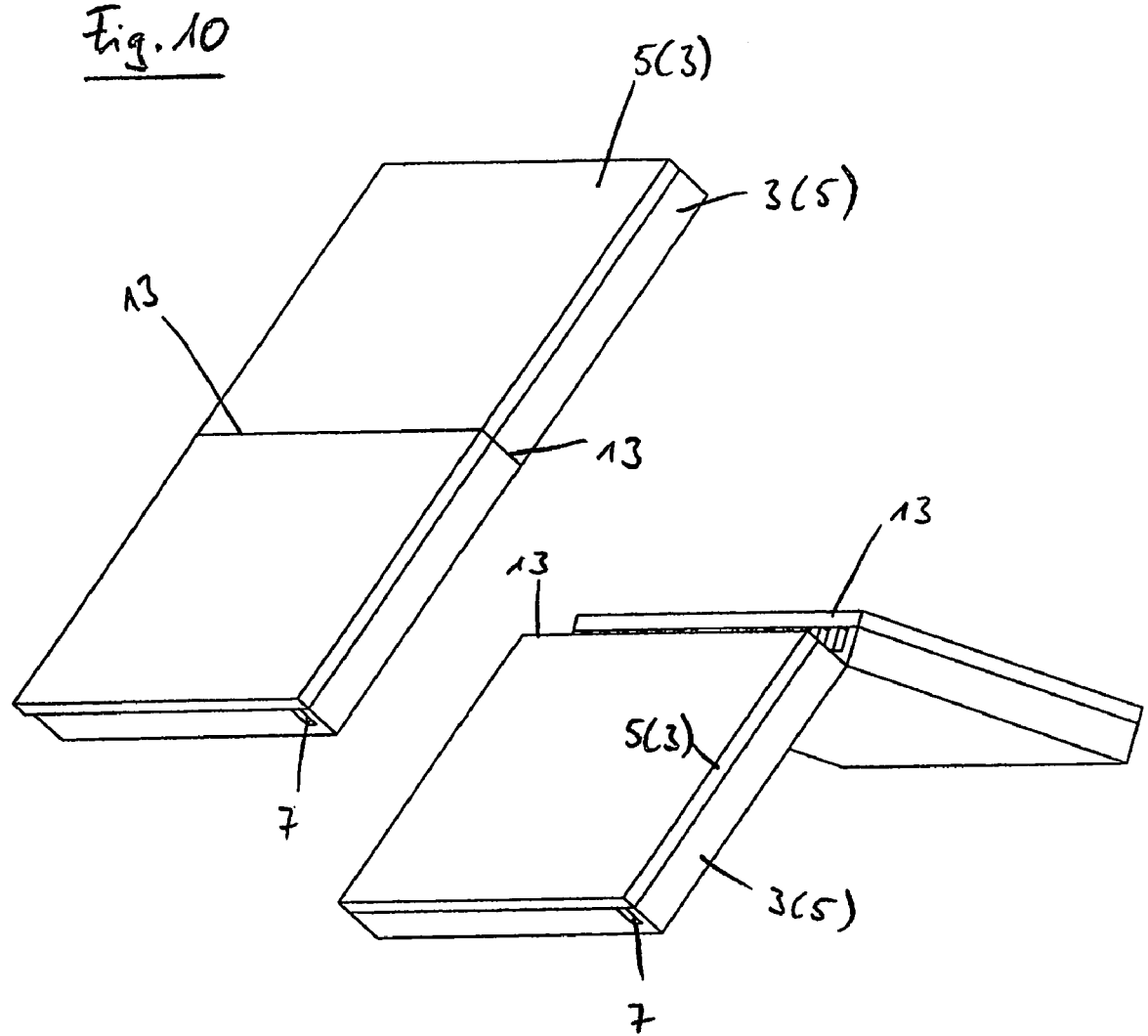

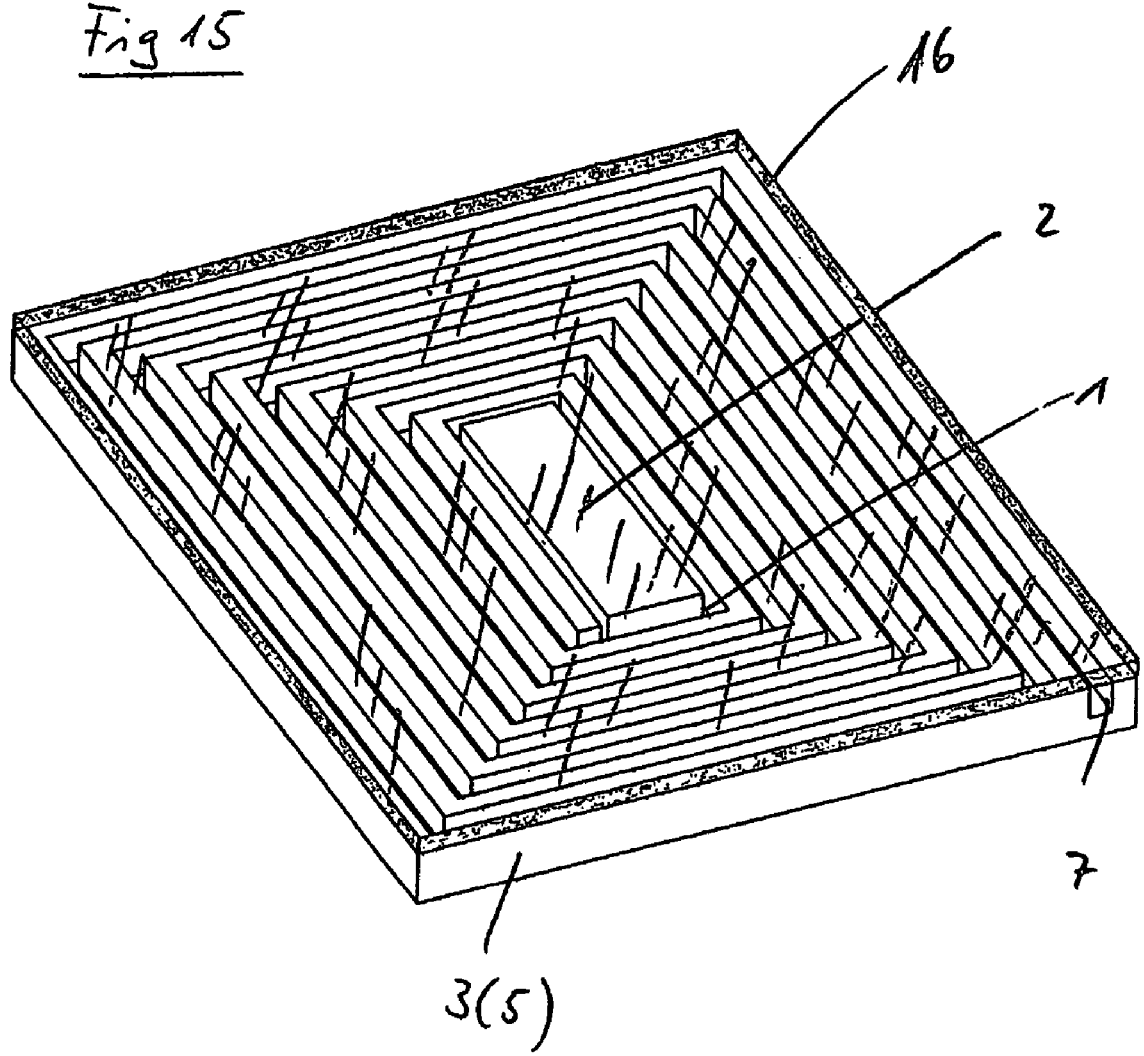

STERILIZATION TESTING DEVICE

BACKGROUND OF THE INVENTION

Figure 1:
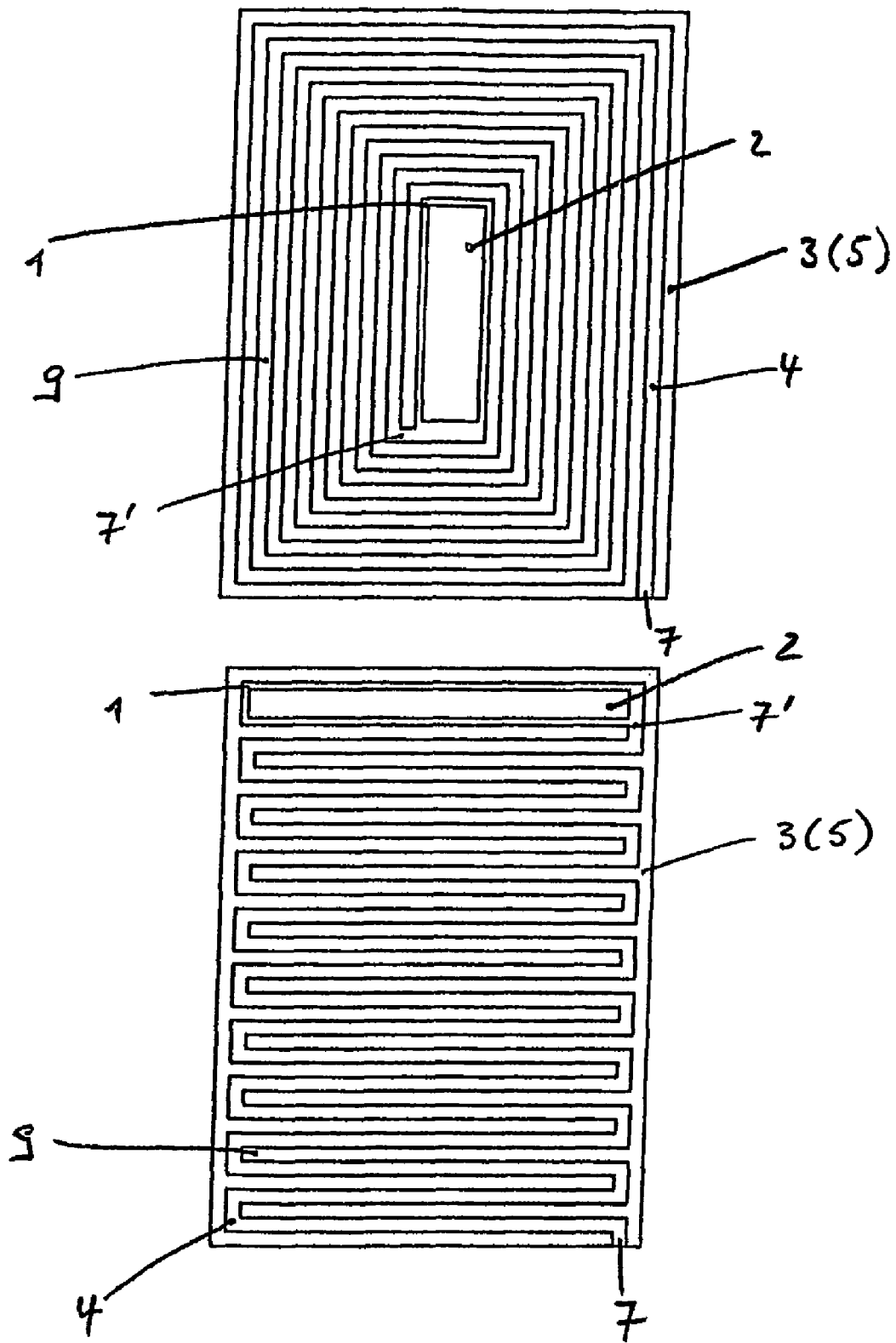

The invention relates to a sterilization testing apparatus comprising a housing with a testing chamber, an indicator placed therein, and a supply line for supplying the sterilizing medium.

Sterilization apparatuses are used to be able to decide with adequate certainty after a sterilization whether the sterilization procedure was successful.

Preferably a gaseous or vaporous medium is provided as the sterilization medium, e.g., steam, ethylene oxide, or formaldehyde. In particular with so-called steam sterilizers like those employed in hospitals, long tubes and medical tools and equipment must be able to be sterilized with a probability approaching certainty. In the case of steam sterilizers, as a rule the sterilizer is evacuated prior to supplying the e.g. normally 121° C. or 134° C. hot saturated steam. The effect of this is that the sterilization agent travels unimpeded through the residual gases remaining in the sterilization item to the locations to be sterilized. For this, it is necessary that the testing chamber with the indicator is connected to the atmosphere of the steam sterilizer only via a supply line that is very long relative to its cross-section.

The coupling of the supply line to the testing chamber represents a weak point in the sterilization testing apparatus.

Thus, in accordance with DE 43 19 397 C1 it is established that given the aforesaid conditions damage to the supply line is conceivable. The damage can begin at the connection or coupling between supply line and testing chamber. Even minor leaks can be sufficient for the path of the ambient sterilization atmosphere to be shortened, while circumventing the longer path through the supply line, so that the indicator located in the testing chamber incorrectly indicates complete sterilization and/or adequate sterilization conditions.

The connection from the supply line to the testing chamber is also frequently found to be the weak point of the testing system because the supply line hangs loose on the testing chamber and/or its container and this coupling point is mechanically stressed when the testing body is used.

In accordance with DE 43 19 397 C1, for these reasons the supply line embodied as a tube is replaced by a stopper made of porous material that makes it more difficult for the sterilization agent to flow into the testing chamber like a labyrinth seal. When used frequently, this solution has the disadvantage that the stopper acts not only like a labyrinth but also like a barrier to the sterilization agent.

With DE 197 24 158 A1, the described disadvantages are intended to be rectified in that a sterilization testing apparatus is created with a supply means embodied as a long extended tube, whereby the supply line is closely packed—mechanically immobile—on the container. However, the disadvantage of this solution is that the supply line still is not protected from damage, even if it is practically securely connected to the container of the testing chamber and thus the connecting parts are no longer subject to mechanical stress. In addition, producing this proposed solution is very complex.

The known sterilization testing apparatus have an additional disadvantage.

The indicator must be placed in the sterilizer by the operator prior to the sterilization procedure and must be removed again for documentation purposes after the sterilization. As a rule, the testing chamber is closed by a cover that can be inserted or screwed on. These covers generally have a seal that is intended to prevent the short-circuit of the surrounding sterilization agent and testing chamber and must be tested regularly and replaced if necessary. If the cover and/or the seal has a leak, it is not possible to check whether the indicator is displaying successful sterilization due to the leak in the cover or the seal or due to correct sterilization. Likewise, it is possible that the indicator is pinched between the testing chamber wall and the cover when the cover is screwed or placed on.

With sterilization apparatus, it is necessary that an indicator is connected to the atmosphere of the sterilizer only through a supply line that is very long relative to its cross-section. Using the interaction of the sterilization medium, with a supply line that is very long relative to its cross-section, with the indicator it can be demonstrated in models that even hollow spaces and tubes or porous materials are acted upon or penetrated with the sterilization medium.

In DE 102 13 066 A1, a solution for such a sterilization apparatus is proposed in which a hollow diffusion space is formed from two thin films (wall elements) by a protuberance, at least in one of the films, and the second film closes off this hollow diffusion space from the outside so that it is sterilization medium-tight. An indicator is arranged in the hollow diffusion space.

These solutions provide a number of advantages over the existing systems. For one thing, there is no coupling point between testing chamber and supply line, and for another thing it is designed as a disposable item, which greatly simplifies handling of the system.

The disadvantage of this solution is that the supply line tube, in this case called the hollow diffusion space, is subjected to mechanical influences in the sterilization chamber with no protection. The effect of even such a very slight porosity of the hollow diffusion space is that the sterilization medium travels to the indicator, having circumvented the complete path via the entire diffusion segment.

Another disadvantage is that the indicator cannot be removed from the testing body. Although DE 102 13 066 A1 does describe that the complete system is to be archived, given the dimensions as suggested in prEN13060: 2002 and/or in EN 867-5 4.5, the testing system is several millimeters thick, so that the testing system is not suitable for complete documentation.

SUMMARY OF THE INVENTION

It is therefore the object of the invention to create a sterilization testing apparatus whose supply line to the testing chamber has the dimensions required for conventional steam sterilization without having the weak points at the coupling point and that at the same time is protected against mechanical effects. In addition to its great compactness, the sterilization testing apparatus should make it possible to open and close the sterilization testing apparatus with no problem for the purpose of removing the indicator. Furthermore, it should be very simple to produce in terms of production engineering, it should make it possible to evaluate the performance of a sterilizer in a simple manner, and it should ensure recoverability for disposable items.

This object is inventively attained in that the sterilization testing apparatus comprises at least two housing parts (3) and (5) that are matched to one another, whereby worked into the housing part (3) is a supply channel (4) that supplies the sterilization medium.

The supply channel (4) is arranged such that it forms the base body of the testing chamber (1). The testing chamber (1) receives the indicator (2) that indicates the conclusion of the sterilization procedure.

The supply channel (4) has an opening (7) and (7') both to the testing chamber (1) and to the outside. Thus the sterilization medium can be conducted in from outside via the supply channel (4) that is open there. The supply channel (4) likewise opens into the testing chamber (1). Connectors and coupling parts are not required.

The supply channel (4) worked into the housing part (3) has any desired cross-section. This can preferably be rectangular or square. Since the supply channel (4) has a very thin cross-section while simultaneously having substantial length relative thereto, it particularly makes sense to embody such a supply channel (4) in a meandering or spiral shape.

Fundamentally the housing parts can be designed selectively such that they provide the option to be opened and closed both prior to and after the sterilization procedure in order to provide access to the indicator (2) or the housing parts (3) and (5) are securely joined to one another. The latter variant represents a particularly advantageous embodiment of the invention. In this case the indicator (2) is already placed in the testing chamber (1) during production of the sterilization testing apparatus so that it is not necessary to open the testing apparatus until after the sterilization procedure has concluded to remove the indicator (2).

In order to be able to make it possible to access the testing chamber (1) for removing the indicator (2), provided in the housing part (3) or (5) is an opening (6) that is closed by means of a closure (12) for those cases in which the housing parts (3) and (5) are securely joined to one another.

Such a closure (12) can be embodied in a particularly advantageous manner as a single use opening. This always makes sense when the two housing parts (3) and (5) are securely joined to one another and thus are likewise provided for single-instance use.

However, the invention also permits additional options to be able to check the indicator (2) for its reaction during single-instance use or multiple use.

Thus, in one additional embodiment of the sterilization testing apparatus, the housing parts (3) and (5) are detachably joined to one another. In such an embodiment, the housing parts (3) and (5) can be opened and closed in a simple manner for placing and/or for removing the indicator (2). Such an embodiment can be manufactured from metal, for instance. A seal (10) should then be placed in an advantageous manner between the housing parts (3) and (5). It has been demonstrated that a sealing mat that is contained in the housing part (5) is particularly suitable for this. Such a sealing mat could comprise for instance silicon material.

In the inventive solution of housing parts (3) and (5) joined securely to one another, it is also possible to do without an opening (6) with a closure (12) in that the sterilization testing apparatus is opened, and thus the indicator (2) can be removed, by breaking the housing parts (3) and (5) at the predetermined breaking line (13).

Likewise for housing parts (3) and (5) that are securely joined to one another it is inventively provided that the housing parts (3) and (5) are produced from a transparent material in order to be able to view the indicator (2) and/or determine its reaction without opening the apparatus or breaking it on a predetermined breaking line (13).

Another embodiment of the sterilization testing apparatus provides that it comprises more than two housing parts (3) and (5) that are matched to one another. This is a so-called multilayer sterilization apparatus. This embodiment provides the option of producing sterilization test apparatus that are shorter in width and length than in height in terms of their physical dimensions.

In this case, the housing part (3") contains the supply channel (4) with an opening (7) that produces a connection to the outside. The housing part (3') also contains a supply channel (4) that is provided with an opening (7') that enables a connection to the testing chamber (1) with an indicator (2) placed therein. Both housing parts (3') and (3") are themselves joined to one another by an opening (11).

In the multilayer embodiments, a meandering or spiral (shape) also inventively makes sense in order to be able to house, if needed, the necessary length of the supply channel (4) in particularly small housings (3) and (5) of the sterilization testing apparatus. For the multilayer embodiment, the inventive solutions listed above can be used; these have already been provided and described for single-layer housing parts (3) and (5) that are joined securely to one another.

Advantageously, the housing parts (3) and (5) comprise plastic, whereby each of the housing parts can also comprise different plastic materials. This always makes sense when a transparent plastic material is used so that the indicator (2) can be visible.

It has been demonstrated that the housing parts (3) and (5) made of a heat-resistant plastic that is suitable for an injection molding process are particularly favorable materials for producing the inventive sterilization testing apparatus.

Alternatively to this solution in which for removing the indicator provided in the housing part (3) or (5) is an opening that must be closed with a single-use closure, in accordance with the invention a variant that is very effective in terms of production engineering is proposed that makes possible a quantitative statement about the sterilization. This variant of the sterilization testing apparatus thus permits not only a statement about whether the sterilization procedure has been completed, but furthermore even provides information about the performance of the sterilizer.

This is inventively attained in that the supply channel (4) that supplies the sterilization medium can be worked into the housing part (3) or into the housing part (5) or into both. Using an at least partially meandering and/or spiral-shaped arrangement of the supply channel, ridges form in the interior of the housing, and these ridges at least partially along with the side part(s) of the housing parts (3) and/or (5) form a part of the supply channel (4). A supply channel (4) formed in this manner receives the indicator (2).

The invention selectively also provides that the supply channel can be arranged such that using this arrangement or at least a part of a side part of the housing part(s) (3) and/or (5) a testing chamber (1) is created in which an indicator (2) can be placed.

The supply channel (4) worked into the housing part (3) and/or (5) has any desired cross-section. Preferably it can be embodied rectangular or square.

A very compact construction is obtained by working the supply channel into the housing part. The supply channel is situated protected in the interior of the housing and is optimally protected against external damage.

In accordance with one preferred embodiment, the supply channel (4) has a length that is so long relative to its cross-section that under normal sterilization conditions the supply channel (4) cannot be completely deaerated.

In this case, it makes sense to place into the complete supply channel one or a plurality of indicators that indicate the precise segment up to which the sterilization medium has penetrated. In other advantageous embodiments the indicator (2) is distributed selectively over the entire length of the supply channel or a plurality of indicators (2) is distributed over the length of the supply channel (4).

This embodiment is suitable for instance for periodic tests of the sterilizer, since in contrast to conventional sterilization testing apparatus it provides a quantitative statement about the maximum segment for which sterilization is attainable for instance for a tube with uniform diameter and it is possible to detect trends in the performance of the sterilizer early on. For this, it makes sense to apply a type of scale to the housing in order to be able to read and document the values with certainty. In this case, the housing should be produced from a transparent material so that the result can be read directly. In this aforesaid embodiment it also makes sense that the sterilization testing apparatus comprises more than 2 housing parts (3) and (5) that are matched to one another. Thus, this is a multilayer sterilization testing apparatus that is shorter in width and length than in height in terms of its physical dimensions.

A sterilization testing apparatus employed for disposable use is inventively provided with a machine-readable continuous code, since in this manner clear recoverability of the testing systems is provided up to the production process for the testing apparatus.

Advantageously, the housing parts (3) and (5) likewise comprise plastic, whereby each of the housing parts can also comprise different plastic materials. This always makes sense when a transparent plastic material is used so that the indicator (2) is visible through the housing parts (3) and/or (5). It has been demonstrated that the housing parts (3) and (5) made of a heat-resistant plastic that is suitable for an injection molding process are particularly favorable materials for producing the inventive sterilization testing apparatus.

Selectively the housing parts can also be designed such that they offer the option of opening and closing both before and after the sterilization procedure so that the indicator (2) can be accessed or the housing parts (3) and (5) are securely joined to one another.

In the latter case, the ridge(s) (9) and the housing parts (3) and (5) the supply channel (4) are embodied such that they close sterilization media-tight to the outside and to themselves.

In the embodiment in which the housing parts are securely joined to one another, selectively worked into the housing part (3) or (5) is a tear strip (14) that, by tearing it, permits the housing part (3) or (5) to be opened and the indicator (2) to be removed.

Another particularly preferred embodiment is comprised for the case in which the housing part (3) or (5) that does not contain the ridge(s) (9) represents a film (16). Such a solution represents a particularly cost-effective variant of the invention.

The particular advantage of the inventive solution is comprised in producing a very cost-effective sterilization testing apparatus, since the latter can be produced in very high numbers. There is the possibility of designing the invention such that it can be employed for single use or multiple use.

One particular advantage is attained in the utilization of the sterilization testing apparatus in single use, however. An exceptionally compact apparatus results that offers particular protection from external influences. Since in the field of sterilization a great deal of value must be placed on certainty and in particular there must be as few sources of errors as possible for personnel, this compact solution is a preferred embodiment. The greatest possible certainty is attained with the compact sterilization testing apparatus in that hospital personnel cannot have any effect on the testing apparatus prior to or after the sterilization procedure by opening and closing the apparatus.

The personnel need only place the sterilization testing apparatus into the sterilization machines and, after the sterilization cycle, either actuate the single-use opening for the purpose of removing the indicator or read the results of the sterilization from the indicator through the transparent half of the housing.

Figure 2:
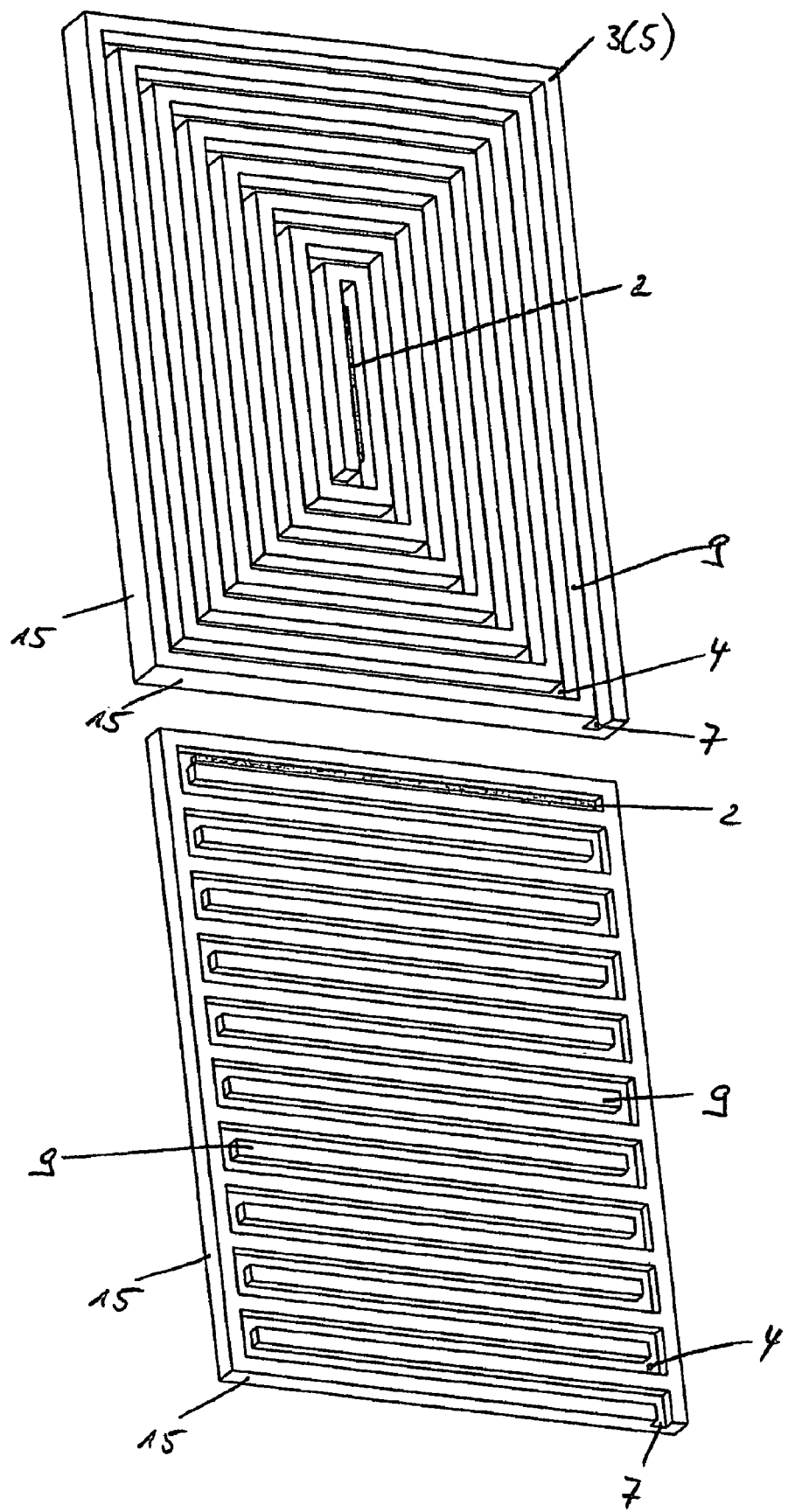
Figure 3:
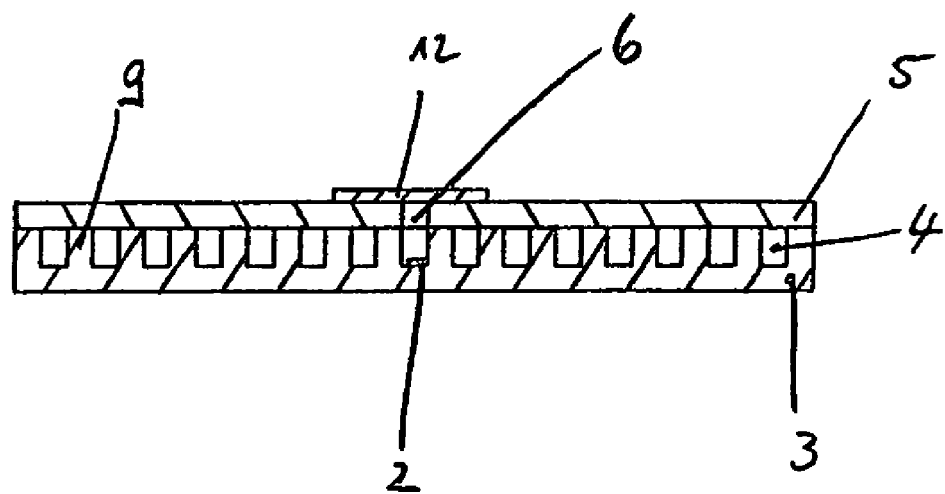
Figure 4:
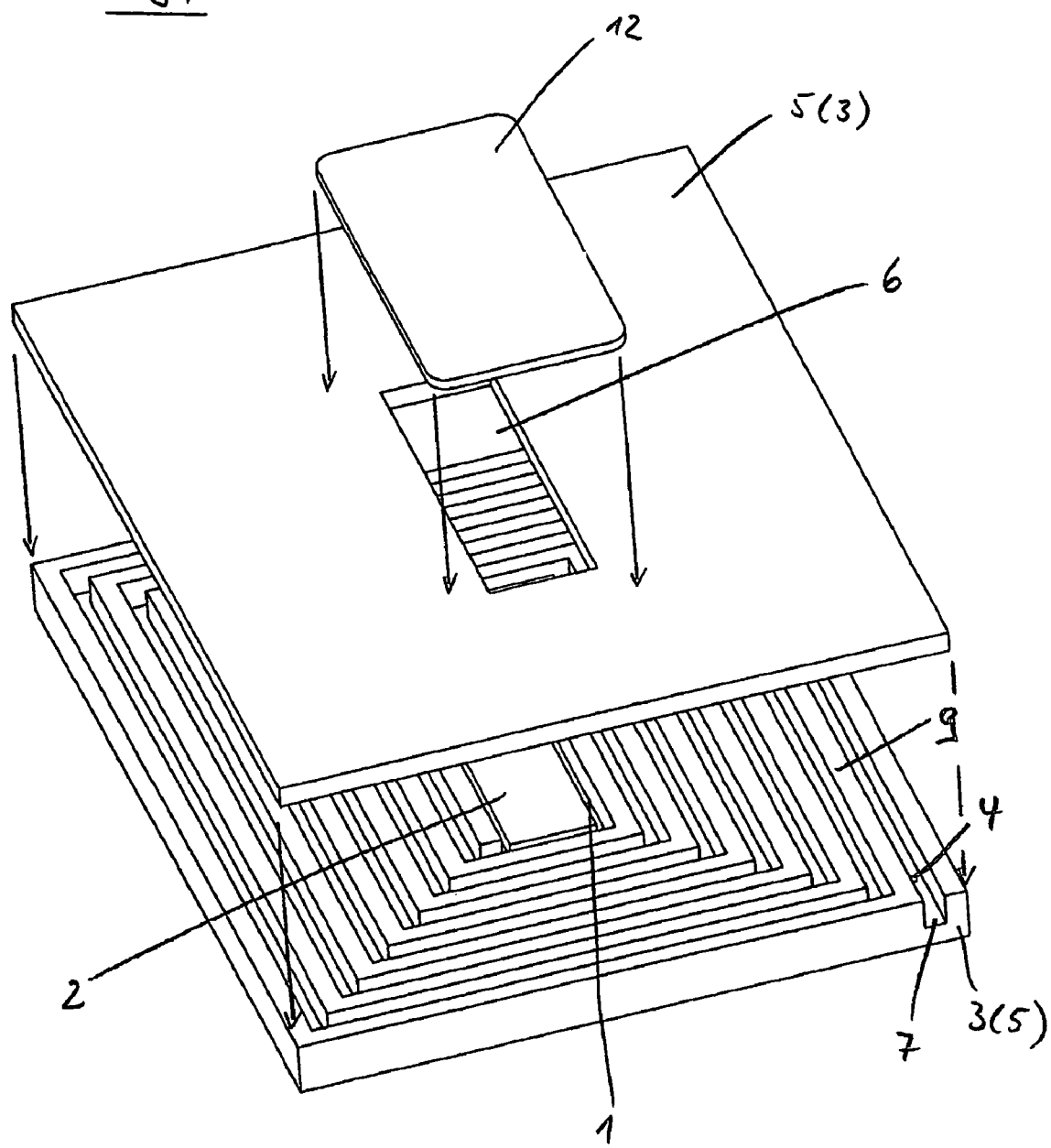
Figure 5:
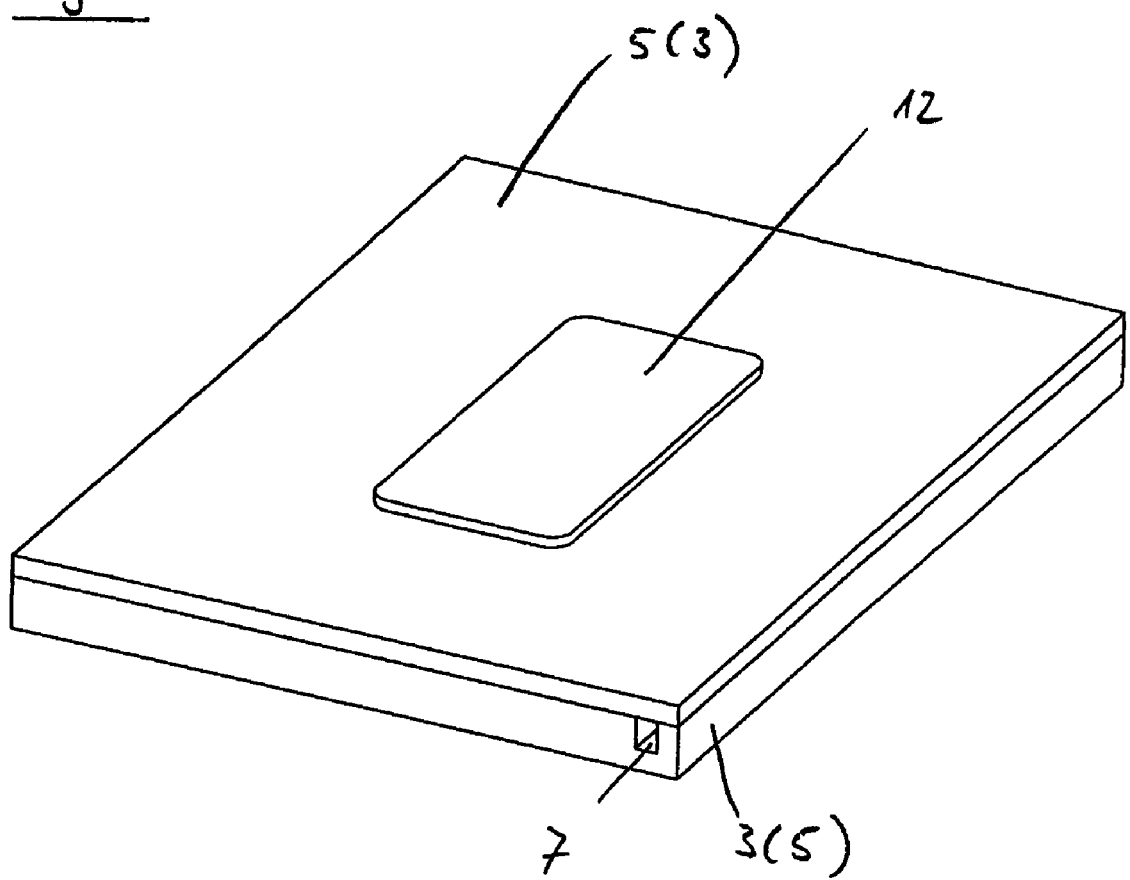
Figure 6:
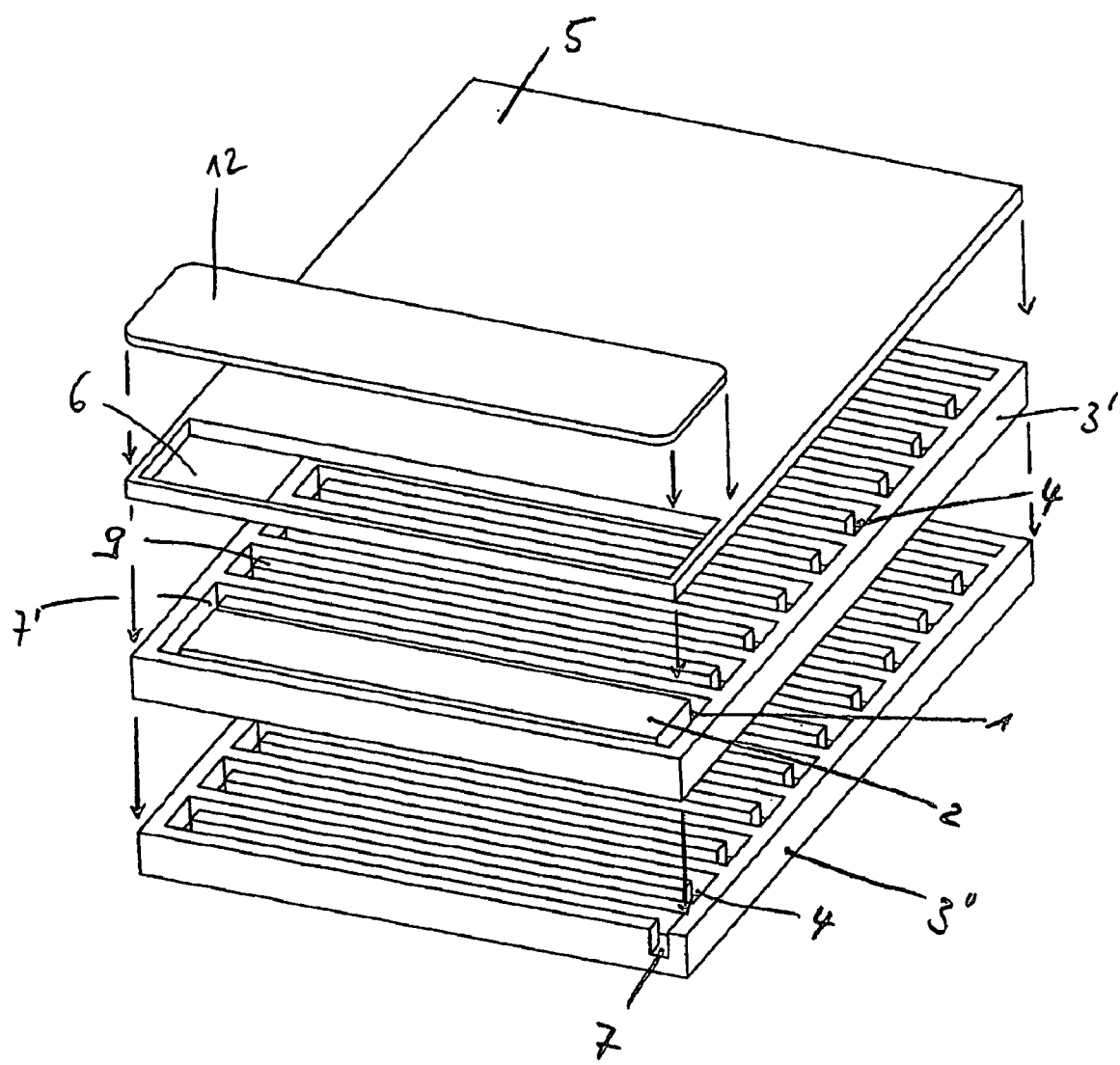
Figure 7:
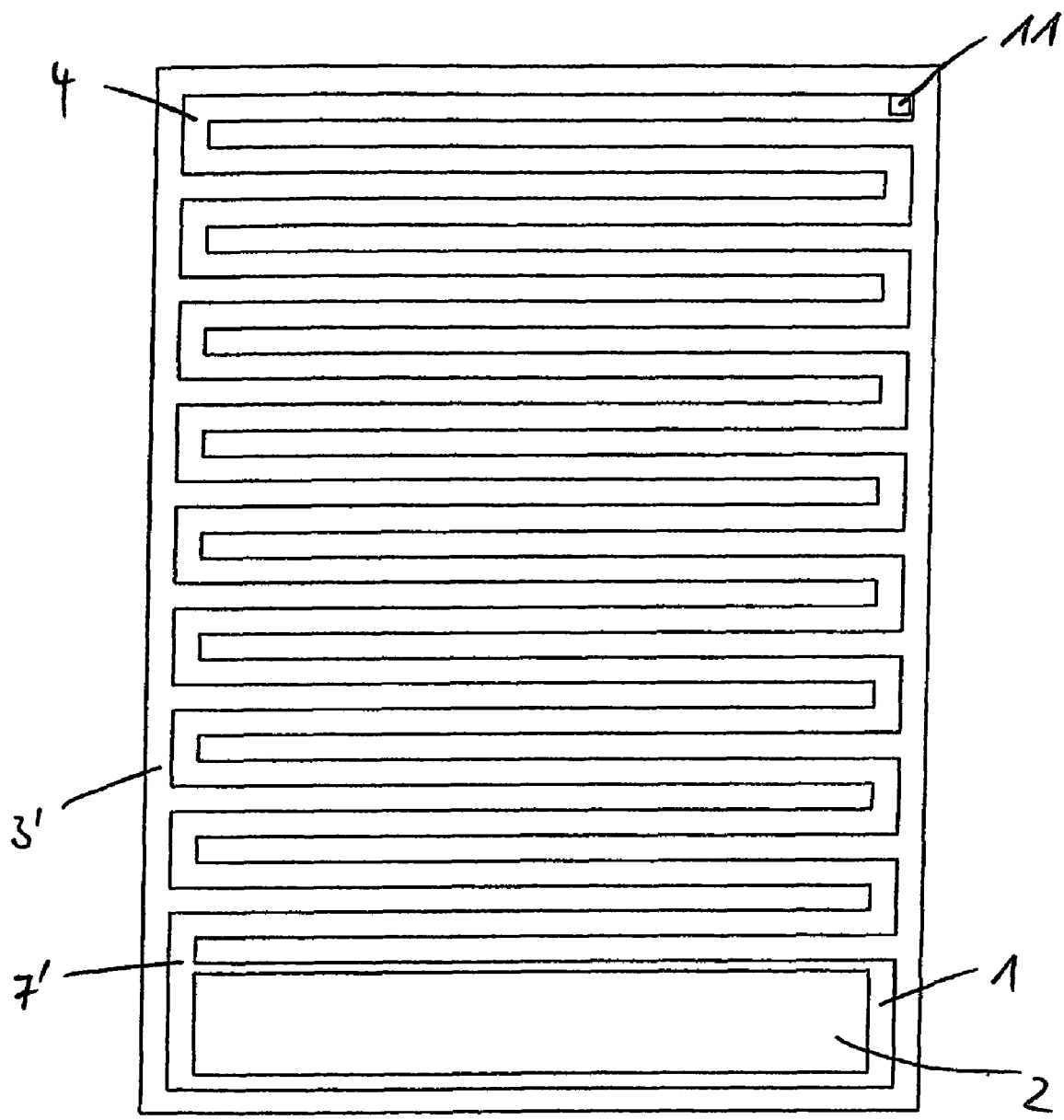
Figure 11:
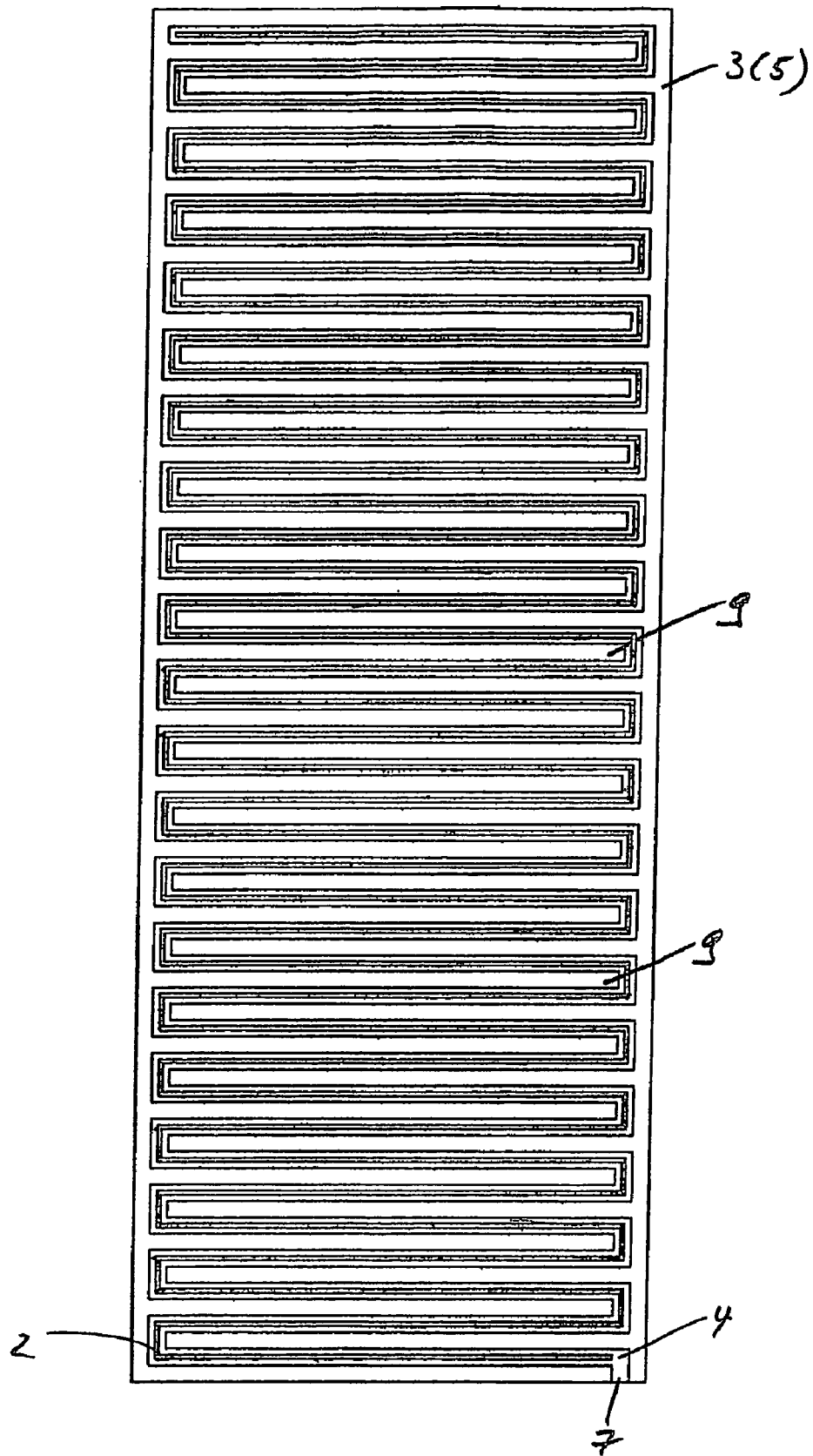
Figure 12:
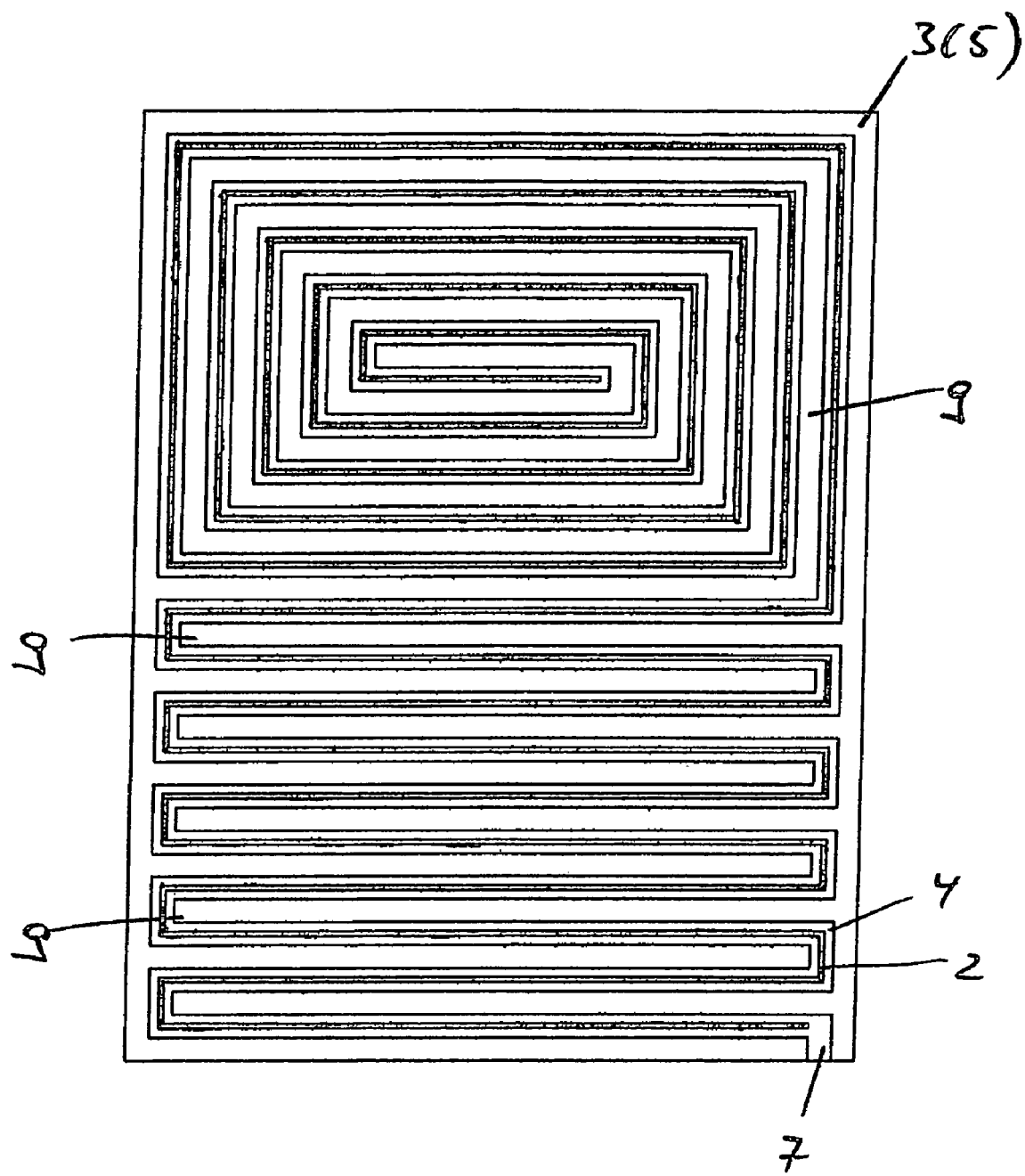
Figure 13:
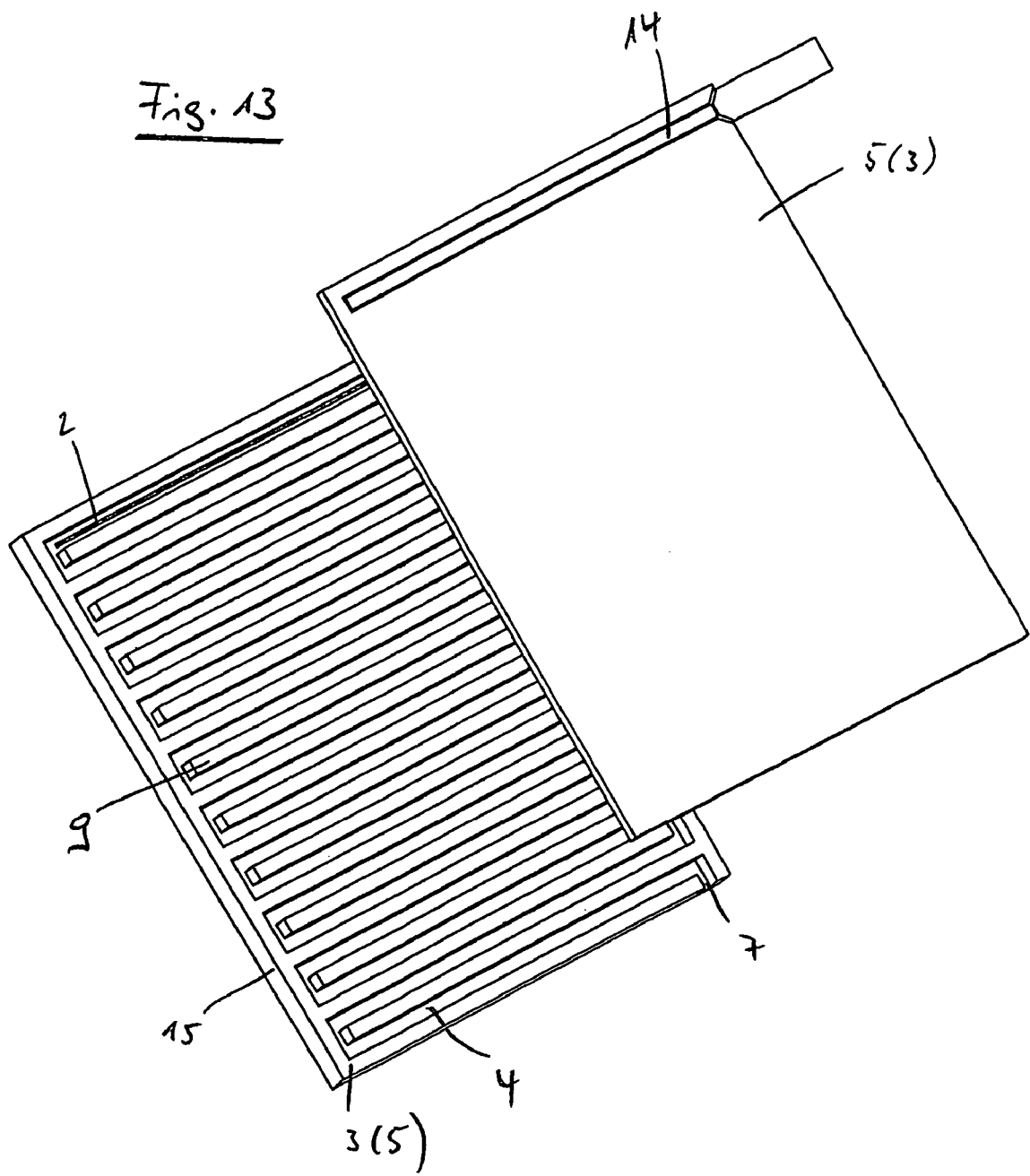
Figure 14:
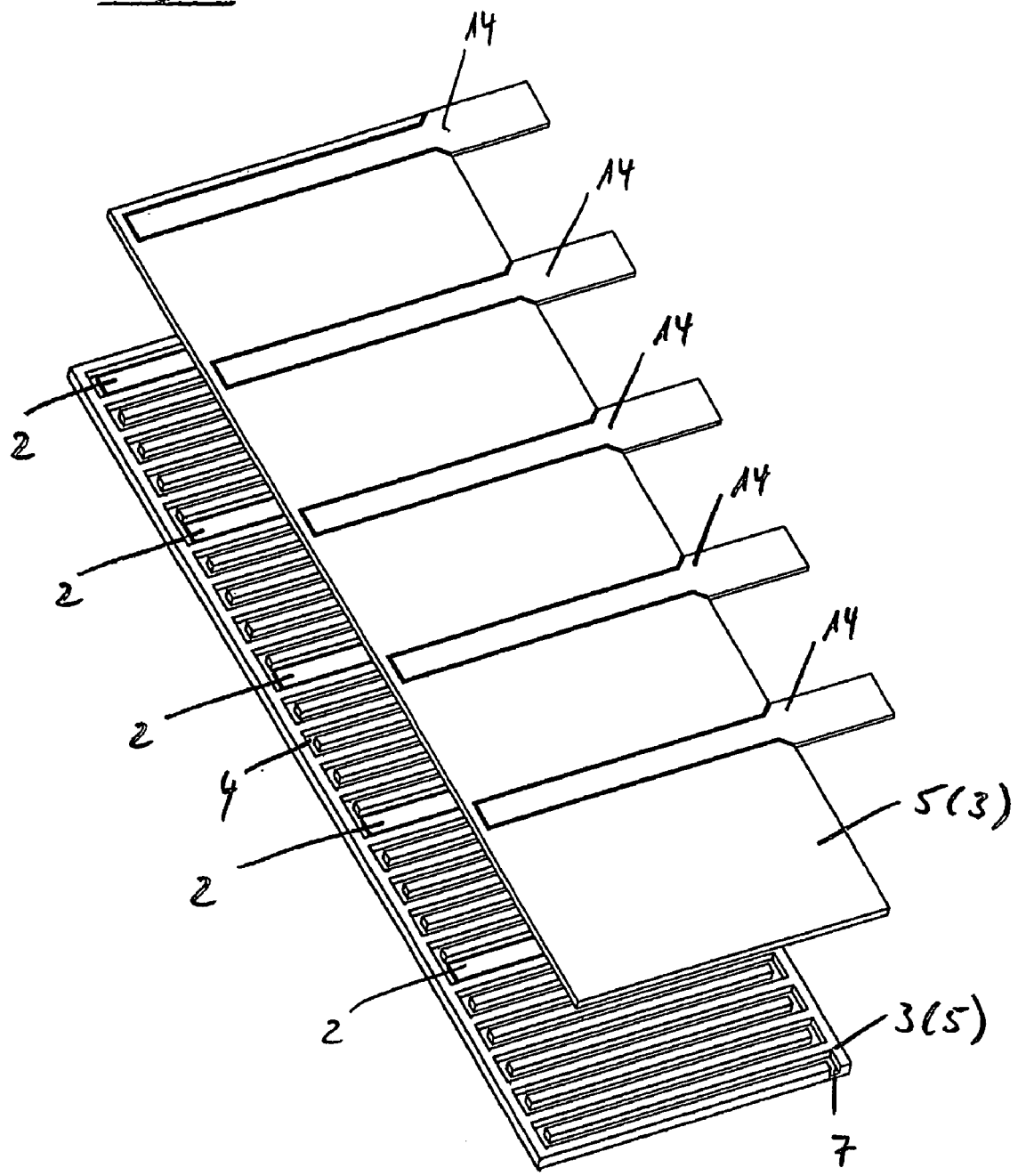

The inventive solution is illustrated using drawings in FIG. 1 through FIG. 15 to provide a more detailed explanation.

BRIEF DESCRIPTION OF THE DRAWINGS (FIG. 1) A top view of the housing part (3)/(5) without corresponding housing part (5)/(3) with spiral-shaped or meandering supply channel (4), embodied testing chamber (1) with indicator (2) placed therein.

(FIG. 2) illustrates a housing part (3) or (5) into one of which a spiral-shaped supply channel (4) is worked and into one of which a meandering supply channel (4) is worked and at least one ridge (9) is formed by these supply channels (4). It is also very easy to see how the supply channel (4) is formed by the housing side parts (15) and the ridge(s) 9.

(FIG. 3) illustrates a sectional illustration of a sterilization testing apparatus with a spiral-shaped supply channel (4) worked into the housing (3) that is securely joined to a housing part (5) and the housing part (5) has an opening (6) that is closed by a closure (12). The indicator (2) is placed directly into the supply channel (4).

(FIG. 4) is an exploded illustration of a sterilization testing apparatus with a spiral-shaped supply channel (4) in the housing part (3) or (5). The housing part (5) or (3) has an opening (6) that is closed with a closure (12). The indicator (2) in the testing chamber (1) is accessed by opening the closure (12).

(FIG. 5) illustrates (FIG. 4) as assembled.

(FIG. 6) illustrates a multilayer sterilization apparatus.

(FIG. 7) is a top view of the housing part 3' with opening (11).

(FIG. 8) is a variant of a multiuse sterilization testing apparatus in which unintentional opening of the housing parts (3) and (5) is prevented by clamps (8).

(FIG. 9) is a variant of a multiuse sterilization testing apparatus, whereby the housing part (3) and the seal (10) are inserted into the housing part (5).

(FIG. 10) is a single-use sterilization testing apparatus in which the housing parts (3) and (5) are broken on the predetermined breaking line (13) in order to remove the indicator (2).

(FIG. 11) illustrates a sterilization testing apparatus in which it is schematically illustrated that a supply channel (4) is worked in that is very long compared to its cross-section and that under normal sterilization conditions cannot be completely deaerated. In this case the indicator (2) is placed over the complete length of the supply channel (4) in order to check the extent to which the sterilization medium has penetrated in the supply channel (4).

(FIG. 12) illustrates a partially meandering and spiral-shaped embodiment of the supply channel (4). The indicator (2) in this case is placed in the complete supply channel (4).

(FIG. 13) is an exploded drawing illustrating how the housing part (5) or (3) can be opened using a tear strip (14) in order to be able to remove the indicator (2).

(FIG. 14) is an exploded drawing of a sterilization testing apparatus in which a plurality of indicators (2) is placed in the housing part (3) or (5). The individual indicators (14) [sic] can be removed by opening the tear strips (14).

(FIG. 15) illustrates one preferred embodiment in which the supply channel (4) is worked into the housing part (3) or (5) and the housing part (5) or (3) is sealed with a transparent film (16).

IN THESE FIGURES (1) Test chamber
(2) Indicator
(3) Lower housing part
(3') Housing part in multilayer embodiment
(3") Housing part in multilayer embodiment
(4) Supply channel
(5) Upper housing part
(6) Opening in the housing part (3), (5)
(7) Opening on supply channel (4)
(7') Opening on supply channel (4) to testing chamber (1)
(8) Clamps
(9) Ridge(s)
(10) Seal
(11) Opening between (3') and (3")
(12) Closure to (6)
(13) Predetermined breaking line
(14) Tear strip
(15) Housing side part
(16) Film

DETAILED DESCRIPTION OF THE INVENTION

The invention is explained in the following using several exemplary embodiments.

One preferred embodiment is comprised in that the housing parts (3) and (5) are made of a heat-resistant and mechanically resistant plastic material and are produced in an injection molding process. The housing part (5) has an opening (6) that is closed with a single-use closure (12). The single-use closure (12) comprises a mechanically resistant and heat-resistant film that during production is stamped gas-tight and thus closes off access to the testing chamber (1).

The housing parts (3) and (5) are permanently joined to one another in the production process by ultrasound welding after the indicator (2) has been placed in the testing chamber (1).

After sterilization has been performed the film is torn off to open the sterilization testing apparatus in order to be able to remove the indicator (2) from the testing chamber (1).

Another preferred embodiment of the invention provides that the supply channel (4) in the housing part (3) or (5) is arranged such that the supply channel (4) opens into a testing chamber (1) after a certain length. Thereafter the supply channel continues and opens into the next testing chamber. This system of sequential supply channels and testing chambers should be designed to be long enough that under normal sterilization conditions it cannot be completely deaerated. The housing part (3) or (5) can be opened using the tear strips in order to access the indicators. Thus it is possible to determine the length to which the supply channel could be deaerated.

In that the preferred embodiment concerns a disposable item, it has been demonstrated that it is advantageous to be able to uniquely identify the disposable item using a serial number. It has also proved advantageous to encipher the serial number as a bar code.

In another advantageous embodiment of the invention, the supply channel (4) is worked into the housing (3) or (5). The supply channel opens into a testing chamber in which an indicator has been placed. The housing part (3) or (5) is sealed with a transparent film so that reaction of the indicator can be checked through the film and the indicator is accessible by removing the film.

The invention claimed is:

1. Sterilization testing apparatus comprising a housing including a testing chamber having a base portion, a supply line for supplying a sterilizing medium to the testing chamber, at least one indicator located in at least the testing chamber for indicating completion of sterilization, the housing being comprised of an assembly of first and second superimposed housing parts fabricated of metal, injection-moldable plastic, or both, the supply line being comprised of a channel located between a sidewall of the first housing part and at least one ridge positioned on the interior of the first housing part, the sidewall being located at an outer side of the first housing part, the channel providing a flowpath for a sterilizing medium defined by the sidewall and the at least one ridge, the channel covering substantially all of the surface area, including the length and width of the first housing part of the testing apparatus but for a surface portion of the first housing part comprising the testing chamber, an opening provided on the outside of the first housing part communicating with the channel for introducing a sterilizing medium to the housing from a sterilizing medium source located outside the housing, the channel communicating with the testing chamber at a channel end opposite the opening in the first housing part, whereby a sterilizing medium that enters the housing through the opening travels directly to the testing chamber via the channel, wherein the channel has a length that, relative to a cross-section thereof, is sufficiently great to impede complete deaeration of the supply line during sterilization.

2. Sterilization testing apparatus according to claim 1, wherein the indicator is a single indicator which extends over the entire length of the channel.

3. Sterilization apparatus according to claim 1, wherein a plurality of indicators are distributed over the entire length of the channel.

4. Sterilization testing apparatus according to claim 1, wherein, apart from the opening, the housing is hermetically sealed.

5. Sterilization testing apparatus according to claim 1, wherein the channel is of square or rectangular cross-section.

6. Sterilization testing apparatus according to claim 1, wherein the channel provides a spiral or meandering flowpath.

7. Sterilization testing apparatus according to claim 1, wherein the first and second housing parts are fixedly secured together.

8. Sterilization testing apparatus according to claim 7, further comprising a breaking line, along which the first and second housing parts are manually breakable to provide access to the indicator.

9. Sterilization apparatus according to claim 7, further comprising a least one tear strip in the at least one of the first and second housing parts, whereby tearing away of the tear strip provides access to the indicator.

10. Sterilization testing apparatus according to claim 7, further comprising a second opening provided in the second housing part for accessing the indicator, the second opening being provided with an openable closure positioned over the second opening.

11. Sterilization testing apparatus according to claim 10, wherein the closure comprises a film for re-closing the second opening.

12. Sterilization testing apparatus according to claim 1, wherein a plurality of ridges is formed on the first housing part, and the second housing part is provided with a flat surface on a side facing the first housing part.

13. Sterilization testing apparatus according to claim 1, wherein the second housing part comprises a transparent material providing visual inspection of the indicator without opening the housing.

14. Sterilization testing apparatus according to claim 1, further comprising a scale applied to at least one of the first and second housing parts.

15. Sterilization testing apparatus according to claim 1, wherein the housing is comprised of an assembly of first, second, and third superimposed housing parts in which at least the second housing part is provided with a channel that is superimposed and in communication with the channel of the first housing part.

16. Sterilization testing apparatus according to claim 1, wherein the first and second housing parts are detachable from each other and further comprising a seal positioned between the first and second housing parts that seals the channel off from the external environment.

17. Sterilization testing apparatus according to claim 16, wherein the seal comprises a mat.

18. Sterilization testing apparatus according to claim 1, wherein the first and second housing parts comprise at least one injection molded plastic having a heat resistance of at least 121° C.

19. Sterilization testing apparatus according to claim 1, wherein the second housing part is box-shaped, having an open side positioned between a top surface and a bottom surface of the second housing part, the first housing part being inserted into the second housing part through the open side, whereby the first housing part is retained within the second housing part, the opening of the first housing part being positioned along the open side of the second housing part, a sealing mat positioned between a top surface of the first housing part and a bottom of the top surface of the second housing part, whereby the mat provides a seal between the first and second housing parts.

20. A sterilization testing apparatus comprising:
a housing including a testing chamber having a base portion;
a supply line for delivering a sterilizing medium to the testing chamber;
at least one indicator located in at least the testing chamber for indicating completion of sterilization; wherein
the housing comprising separate first and second superimposed housing parts fabricated of metal, injection-molded plastic having a heat resistance of at least 121° C., or both, which first and second housing parts do not share a common edge or surface prior to being superimposed, and wherein upon superimposing the first and second housing parts, the first and second housing parts share an edge at a housing perimeter;
the supply line being comprised of a channel located between a sidewall provided on an outer side of the first housing part and at least one inwardly facing ridge provided on the second housing part, the channel having an opening at one end thereof communicating with the testing chamber and an opening at the other end thereof for communicating with a source of the sterilizing medium outside the housing and wherein a sterilization medium that enters the housing through the opening travels directly to the testing chamber via the channel, which channel covers substantially all oldie surface area, including the length and width of the first housing part of the testing apparatus, but for a surface portion of the first housing part comprising the testing chamber.

21. The sterilization testing apparatus of claim 20 wherein the first housing part is provided with at least one inwardly facing ridge, whereby the channel is positioned between the sidewall provided on the outer side of the first housing part, the at least one inwardly facing ridge provided on the second housing part, and the at least one inwardly facing ridge of the first housing part.

\* \* \* \* \*